United States Patent
Kohgo et al.

(10) Patent No.: US 10,117,731 B2
(45) Date of Patent: Nov. 6, 2018

(54) MATERIAL FOR DENTURE BASE, DENTURE BASE, METHOD OF MANUFACTURING THE DENTURE BASE, PLATE DENTURE, AND METHOD OF MANUFACTURING THE PLATE DENTURE

(71) Applicants: Mitsui Chemicals, Inc., Tokyo (JP); NITTO JUSHI KOGYO CO., LTD., Tokyo (JP)

(72) Inventors: Osamu Kohgo, Yokohama (JP); Naoyuki Kato, Chiba (JP); Maho Okumura, Ichihara (JP); Ahmad Jalaludin, Chiba (JP); Kouya Kojima, Urayasu (JP); Eizaburo Higuchi, Tokyo (JP); Yuji Takahashi, Tokyo (JP)

(73) Assignees: Mitsui Chemicals, Inc., Tokyo (JP); NITTO JUSHI KOGYO CO., LTD., Tokyo (JP)

( * ) Notice: Subject to any disclaimer, the term of this patent is extended or adjusted under 35 U.S.C. 154(b) by 0 days.

(21) Appl. No.: 15/116,124

(22) PCT Filed: Feb. 4, 2015

(86) PCT No.: PCT/JP2015/053129
§ 371 (c)(1),
(2) Date: Aug. 2, 2016

(87) PCT Pub. No.: WO2015/119163
PCT Pub. Date: Aug. 13, 2015

(65) Prior Publication Data
US 2017/0071708 A1  Mar. 16, 2017

(30) Foreign Application Priority Data

Feb. 5, 2014  (JP) .................. 2014-020634
Dec. 26, 2014  (JP) .................. 2014-265370

(51) Int. Cl.
*A01N 59/16* (2006.01)
*A01N 25/10* (2006.01)
(Continued)

(52) U.S. Cl.
CPC .......... *A61C 13/01* (2013.01); *A61C 13/0004* (2013.01); *A61L 27/16* (2013.01);
(Continued)

(58) Field of Classification Search
None
See application file for complete search history.

(56) References Cited

U.S. PATENT DOCUMENTS 3,427,274 A * 2/1969 Cornell ................. C08F 279/02
106/35
4,396,377 A * 8/1983 Roemer ................. A61K 6/083
433/199.1
(Continued)

FOREIGN PATENT DOCUMENTS

CN  102811694  12/2012
EP  2564807  3/2013
(Continued)

OTHER PUBLICATIONS

International Search Report dated Mar. 3, 2015 filed in PCT/JP2015/053129.
(Continued)

*Primary Examiner* — Peter A Salamon
(74) *Attorney, Agent, or Firm* — Rankin, Hill & Clark LLP

(57) ABSTRACT

Disclosed is a material for a denture base containing a polymer component having a weight average molecular weight of 1,200,000 or more and containing an acrylic resin.

27 Claims, 3 Drawing Sheets

(51) Int. Cl.
    *A61K 6/083* (2006.01)
    *A61K 6/00* (2006.01)
    *A61C 13/01* (2006.01)
    *A61C 13/00* (2006.01)
    *A61L 27/16* (2006.01)
    *A61L 27/18* (2006.01)
    *A61L 27/26* (2006.01)
(52) U.S. Cl.
    CPC ............... *A61L 27/18* (2013.01); *A61L 27/26* (2013.01); *A61L 2430/12* (2013.01)

(56) References Cited

U.S. PATENT DOCUMENTS

| | | | | |
|---|---|---|---|---|
| 4,396,476 | A * | 8/1983 | Roemer | A61K 6/083 522/109 |
| 2004/0038178 | A1 | 2/2004 | Torriani | |
| 2012/0296005 | A1 * | 11/2012 | Tanaka | A61L 24/06 523/116 |
| 2013/0101778 | A1 * | 4/2013 | Minakuchi | A61C 13/0022 428/64.1 |
| 2014/0221599 | A1 | 8/2014 | Hishimoto | |
| 2015/0011673 | A1 * | 1/2015 | Yamagawa | C08L 71/00 523/115 |

FOREIGN PATENT DOCUMENTS

| | | | | |
|---|---|---|---|---|
| JP | 656619 | 3/1994 | | |
| JP | 2005538761 | 12/2005 | | |
| JP | 2006521136 | 9/2006 | | |
| JP | 2013144778 | 7/2013 | | |
| WO | 2010058822 A1 | 5/2010 | | |
| WO | 2011090078 A1 | 7/2011 | | |
| WO | WO-2011090078 A1 * | 7/2011 | ............ | A61L 24/06 |
| WO | 2013061462 A1 | 5/2013 | | |

OTHER PUBLICATIONS

Written Opinion of the ISA issued in International Application No. PCT/JP2015/053129 dated Mar. 3, 2015.

Chinese Office Action dated May 2, 2017 issued in the corresponding Chinese patent application No. 201580007102.9 and its partial English translation.

Extended European Search Report dated Aug. 31, 2017 issued in the corresponding European patent application No. 15746884.4.

Taiwanese Office Action dated Jun. 12, 2018 in Taiwanese Patent Application No. 104103834 and its partial English translation.

* cited by examiner

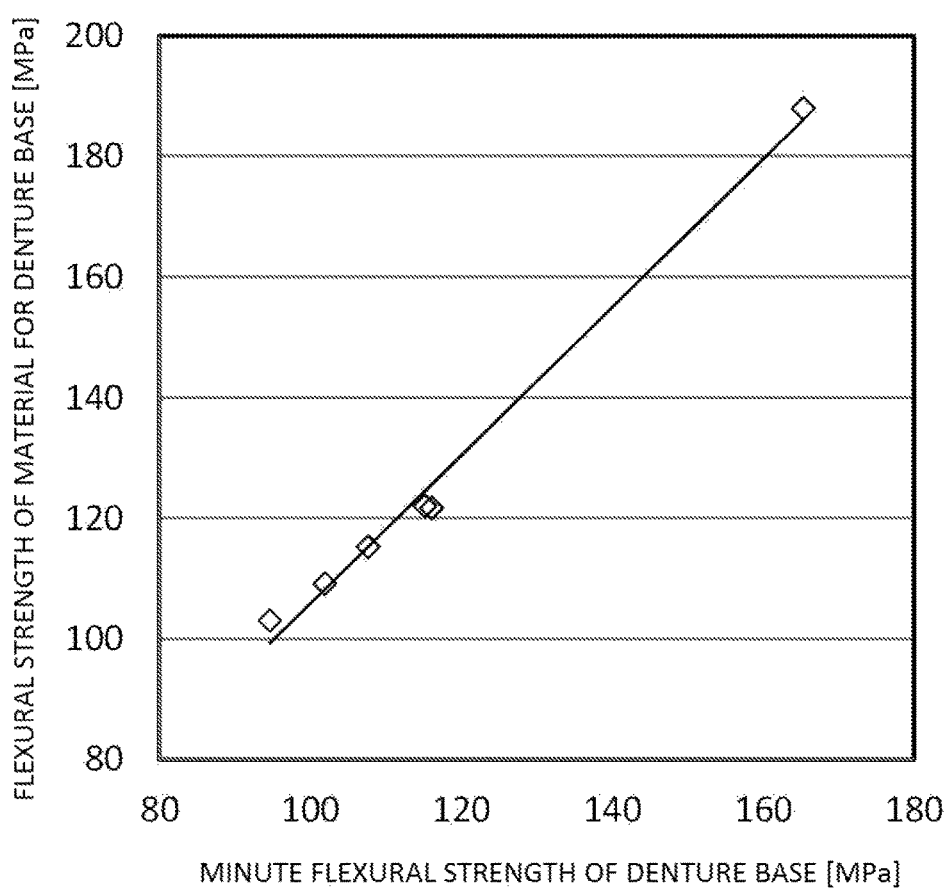

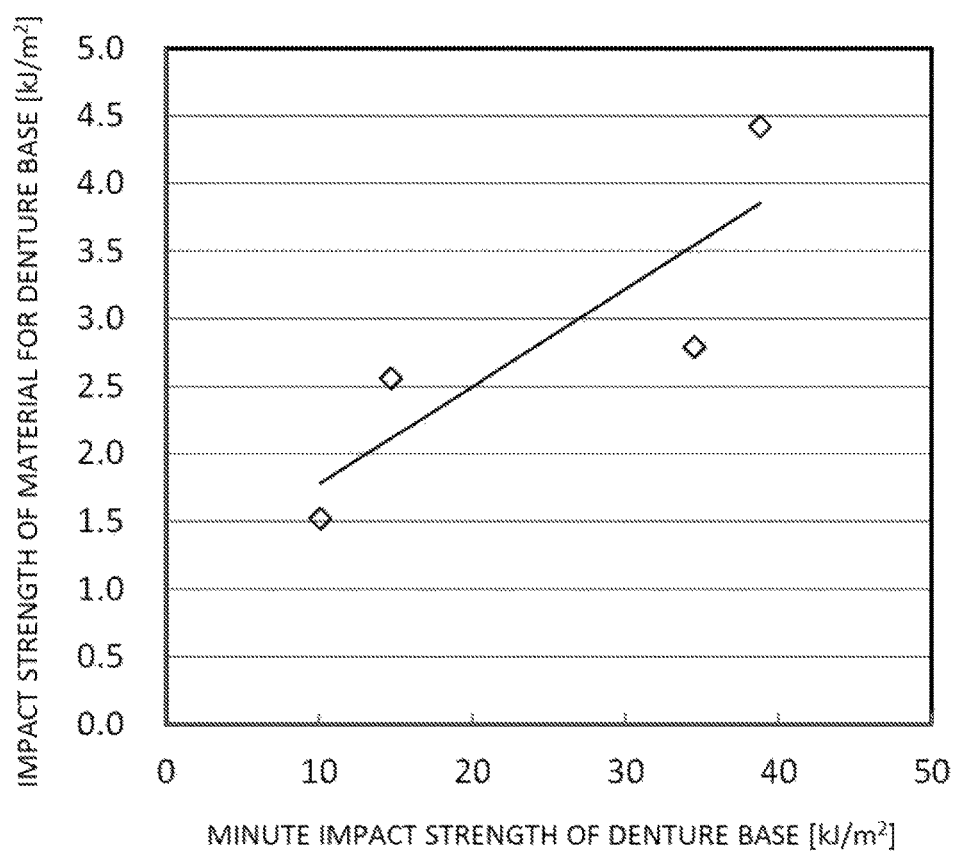

MATERIAL FOR DENTURE BASE, DENTURE BASE, METHOD OF MANUFACTURING THE DENTURE BASE, PLATE DENTURE, AND METHOD OF MANUFACTURING THE PLATE DENTURE

TECHNICAL FIELD

The present invention relates to a material for a denture base, a denture base, method of manufacturing the denture base, a plate denture, and a method of manufacturing the plate denture.

BACKGROUND ART

There has been a widespread use of a plate denture provided with artificial teeth and a denture base for fixing the artificial teeth thereto. As the denture base, a polymer-containing denture base has been widely used.

Conventionally, the polymer-containing denture base has been manufactured by a method of pouring a curable resin into a gypsum mold constituted of an upper mold and a lower mold and then curing the curable resin (by photopolymerization or thermal polymerization, for example).

There has been recently known a method of cutting a cured polymer (resin) with the use of a CAD (Computer Aided Design)/CAM (Computer Aided Manufacturing) system, for example, and thereby manufacturing the above-described denture base (see, for example, WO 2010-058822 and Japanese National-Phase Publication (JP-A) No. 2006-521136).

SUMMARY OF INVENTION

Technical Problem

When a plate denture provided with a polymer-containing denture base is used for a long period of time, the denture base may likely be broken.

According to the consideration made by the inventors of this invention, it was found that an ease of occurrence of the breakage of a denture base is correlated with the durability (yield point strength in a compression test) of the denture base, and as the durability (yield point strength in a compression test) of the denture base becomes higher, the denture base tends to be less likely to be broken.

As a result of further consideration made by the inventors of this invention, it is found out that even when that a hard material (a material having a high elastic modulus) is used as a material for a denture base in order to enhance the durability of a denture base formed of the material, the denture base formed of the material may likely lack durability (yield point strength in a compression test).

In view of the above, an object of the present invention is to achieve the following purposes.

Namely, an object of this invention is to provide a material for a denture base excellent in durability (yield point strength in a compression test) when a denture base is formed of the material.

A further object of this invention is to provide a denture base excellent in durability (yield point strength in a compression test) and a method of manufacturing the denture base.

A furthermore object of this invention is to provide a plate denture, which is provided with a denture base excellent in durability (yield point strength in a compression test) and can prevent the denture base from being broken by use for a long period of time.

Solution to Problem

Specific means for achieving the above objects are as follows.

<1> A material for a denture base containing a polymer component, the polymer component having a weight average molecular weight of 1,200,000 or more and containing an acrylic resin.

<2> The material for a denture base according to <1>, wherein the weight average molecular weight of the polymer component is 1,500,000 or more.

<3> The material for a denture base according to <1> or <2>, wherein the weight average molecular weight of the polymer component is 2,500,000 or more.

<4> The material for a denture base according to any one of <1> to <3>, wherein when the material for a denture base is formed into a test piece having a length of 80 mm, a width of 10 mm, and a thickness of 4 mm, the test piece exhibits 110 MPa or more of flexural strength measured by a three-point flexural test in accordance with JIS K7171 (2008) under conditions of a testing speed of 2 mm/min and a length of a support span of 64 mm.

<5> The material for a denture base according to <4>, wherein the flexural strength is 200 MPa or less.

<6> The material for a denture base according to any one of <1> to <5>, wherein when the material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm, the test piece exhibits 1.41 kJ/m$^2$ or more of impact strength measured by Charpy impact test under the condition of edgewise impact in accordance with JIS K7111-1 (2012).

<7> The material for a denture base according to any one of <1> to <3>, wherein when the material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm, the test piece exhibits 2.0 kJ/m$^2$ or more of impact strength measured by Charpy impact test under the condition of edgewise impact in accordance with JIS K7111-1 (2012), and when the material for a denture base is formed into a test piece having a length of 80 mm, a width of 10 mm, and a thickness of 4 mm, the test piece exhibits 100 MPa or more of flexural strength measured by a three-point flexural test in accordance with JIS K7171 (2008) under conditions of a testing speed of 2 mm/min and a length of a support span of 64 mm.

<8> The material for a denture base according to <8>, wherein the polymer component further contains a rubber.

<9> The material for a denture base according to <8>, wherein the rubber contains a polymer obtained by graft polymerization of a rubbery polymer having a cross-linked structure with a thermoplastic resin component.

<10> The material for a denture base according to <8> or <9>, wherein the rubber contains a polymer obtained by graft polymerization of a butadiene (co)polymer with a thermoplastic resin component.

<11> The material for a denture base according to any one of <8> to <10>, wherein a content of the rubber is from 1% by mass to 10% by mass based on a total amount of the material for a denture base.

<12> The material for a denture base according to any one of <8> to <11>, wherein a content of the rubber is from 1% by mass to 7% by mass based on a total amount of the material for a denture base.

<13> The material for a denture base according to any one of <1> to <12>, wherein a content of the acrylic resin is 90% by mass or more based on a total amount of the material for a denture base.

<14> The material for a denture base according to any one of <1> to <13>, wherein the acrylic resin is a polymer obtained by polymerizing a monomer component containing a monofunctional acrylic monomer in an amount of 95% by mass or more.

<15> The material for a denture base according to <14>, wherein the monofunctional acrylic monomer is at least one selected from the group consisting of methacrylic acid and methacrylic acid alkyl ester.

<16> The material for a denture base according to <14>, wherein the monofunctional acrylic monomer consists of methacrylic acid and methacrylic acid alkyl ester, and an amount of the methacrylic acid based on a total amount of the methacrylic acid and the methacrylic acid alkyl ester is from 0.1% by mass to 15% by mass.

<17> The material for a denture base according to any one of <1> to <15>, wherein the acrylic resin is polymethyl methacrylate.

<18> A material for a denture base, wherein when the material for a denture base is formed into a test piece having a length of 80 mm, a width of 10 mm, and a thickness of 4 mm, the test piece exhibits 110 MPa or more of flexural strength measured by a three-point flexural test in accordance with JIS K7171 (2008) under conditions of a testing speed of 2 mm/min and a length of a support span of 64 mm, and the material for a denture base contains a polymer component that is at least one selected from the group consisting of a sulfone-based resin and an ether ketone resin.

<19> The material for a denture base according to <18>, wherein the flexural strength is 200 MPa or less.

<20> The material for a denture base according to <18> or <19>, wherein when the material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm, the test piece exhibits 1.41 kJ/m$^2$ or more of impact strength measured by Charpy impact test under the condition of edgewise impact in accordance with JIS K7111-1 (2012).

<21> The material for a denture base according to any one of <18> to <20>, wherein the polymer component is at least one selected from the group consisting of polyphenyl sulfone and polyether ether ketone.

<22> The material for a denture base according to any one of <1> to <21>, wherein a content of inorganic fibers and inorganic whiskers is 0.5% by mass or less, based on the total amount of the material for a denture base.

<23> The material for a denture base according to any one of <1> to <22>, wherein the material for a denture base is a block body having a thickness of from 10 mm to 40 mm.

<24> The material for a denture base according to <23>, wherein the material for a denture base is used in manufacturing a denture base by cutting.

<25> A denture base containing the material for a denture base according to any one of <1> to <22>.

<26> A denture base obtained by cutting the material for a denture base according to <23>.

<27> A plate denture comprising the denture base according to <25> or <26> and an artificial tooth fixed to the denture base.

<28> A method of manufacturing a denture base comprising a step of cutting the material for a denture base according to <23> to obtain a denture base.

<29> The denture base manufacturing method according to <28>, wherein the cutting step is a step of cutting the material for a denture base with the use of a CAD/CAM system to obtain a denture base.

<30> A method of manufacturing a plate denture including:
a step of cutting the material for a denture base according to <23> to obtain a denture base; and
a step of fixing an artificial tooth to the denture base.

Advantageous Effects of Invention

The present invention provides a material for a denture base excellent in durability (yield point strength in a compression test) when a denture base is formed of the material.

The invention further provides a denture base excellent in durability (yield point strength in a compression test) and a method of manufacturing the denture base.

The invention furthermore provides a plate denture, which is provided with a denture base excellent in durability (yield point strength in a compression test) and can prevent the denture base from being broken by use for a long period of time.

BRIEF DESCRIPTION OF DRAWINGS

FIG. 2 is a graph showing an example of a relationship between minute flexural strength of a denture base and flexural strength of a material for a denture base in this invention.

FIG. 3 is a graph showing an example of a relationship between minute impact strength of a plate denture and impact strength of a material for a denture base in this invention.

DESCRIPTION OF EMBODIMENTS

Figure 1:
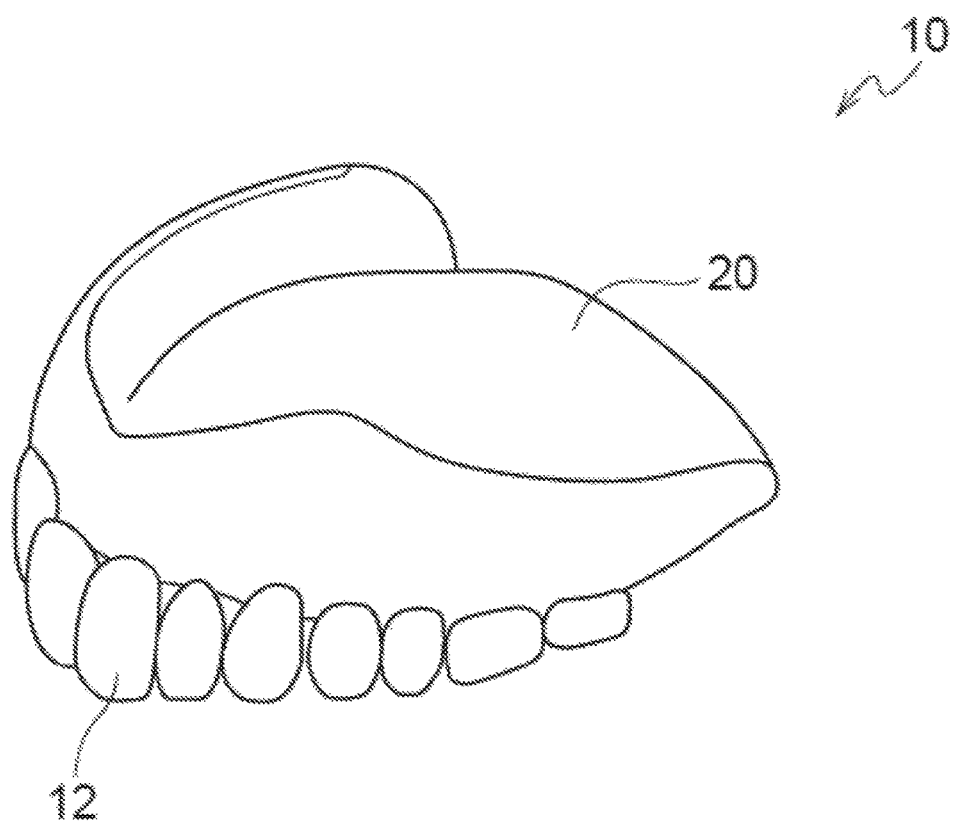
FIG. 1 is a perspective view conceptually showing an example of a plate denture of the present invention.

In this specification, numerical ranges depicted with "from" and "to" represent ranges inclusive of the numbers that respectively appear at the left and right of "to" as the minimum value and the maximum value, respectively. For example, "from a numerical value A to a numerical value B" is synonymous with "a numerical value A or more and a numerical value B or less".

Further, in this specification, yield point strength in a compression test is also merely referred to as "yield point strength". Namely, in the specification, the mere term "yield point strength" means the yield point strength in a compression test.

[Material for Denture Base]

Hereinafter, first and second embodiments of a material for a denture base of the present invention will be described.

<First Embodiment>

A material for a denture base of the first embodiment contains a polymer component having a weight average molecular weight of 1,200,000 or more and containing an acrylic resin.

According to the material for a denture base of the first embodiment, the durability (indicates yield point strength in a a compression test and is hereinafter sometimes referred to as "yield point strength") of a denture base formed of this material is enhanced. Consequently, breakage of the denture base due to use for a long period of time is reduced. Although this reason is not clear, the reason is assumed as follows.

Namely, the denture base has a complex shape corresponding to an oral cavity of a denture user. Thus, according to an occlusal state of the denture user, a force applied to a plate denture is locally concentrated at a portion of the denture base. Therefore, it is considered that even when a hard material (a material having a high elastic modulus) is used as a material for a denture base, the denture base may be broken. Further, it is also considered that a minute clack occurs in the denture base due to some cause during use, the denture base is likely to be broken from the crack as a starting point.

Regarding those points, when as a material for a denture base, it is considered that when there are used not merely a "hard material" (a material having a high elastic modulus) but also a material having high durability against multidirectional forces or a material in which crack hardly occurs even when multidirectional forces are applied thereto, that is, a material in which the flexural strength in a three-point flexural test (hereinafter also referred to as the "flexural strength") is high, the durability (yield point strength) of a denture base formed of this material can be enhanced, and furthermore, when a plate denture is used for a long period of time, a denture base of the plate denture can be prevented from being broken.

Regarding the flexural strength, the present inventors found that a material for a denture base containing a polymer component having a weight average molecular weight of 1,200,000 or more and containing an acrylic resin exhibits high flexural strength.

Thus, according to the material for a denture base of the first embodiment, it is considered that the durability (yield point strength) of a denture base formed of this material can be enhanced, and furthermore, when a plate denture is used for a long period of time, a denture base of the plate denture can be prevented from being broken.

Further, according to the material for a denture base of the first embodiment, since the durability (yield point strength) of a denture base formed of this material can be enhanced, it is possible to manufacture a thin denture base (that is, a lightweight denture base excellent in wearing feeling) as compared to denture bases manufactured by a conventional method using a gypsum mold.

Here, the "flexural strength in a three-point flexural test" of a material for a denture base indicates flexural strength measured by a three-point flexural test in accordance with JIS K7171 (2008) under the conditions of a testing speed of 2 mm/min and a length of the support span of 64 mm when the material for a denture base is formed into a test piece having a length of 80 mm, a width of 10 mm, and a thickness of 4 mm (the same is applied to the following description).

The flexural strength in the three-point flexural test can be measured using a 5-hook flexural test machine model 2001-5 manufactured by Intesco Co., Ltd., for example.

The test piece can be taken from the material for a denture base of the first embodiment by cutting or the like.

Hereinafter, the "flexural strength in a three-point flexural test" is also merely referred to as "flexural strength".

Further, hereinafter, "a length of 80 mm, a width of 10 mm, and a thickness of 4 mm" is also referred to as "80 mm×10 mm×4 mm size".

The weight average molecular weight (Mw) of the polymer component in the first embodiment is 1,200,000 or more.

When Mw of the polymer component is 1,200,000 or more, the flexural strength of a material for a denture base is enhanced, and furthermore, the durability (yield point strength) of a denture base formed of this material is enhanced.

Further, when Mw of the polymer component in the first embodiment is 1,200,000 or more, it is advantageous in cutting workability when a denture base is manufactured by cutting (for example, it is advantageous in that at least one of cracking and chipping is reduced during cutting).

In view of further enhancement of the flexural strength, the Mw of a polymer component is preferably 1,500,000 or more, more preferably 2,000,000 or more, still more preferably 2,500,000 or more, even more preferably 3,000,000 or more, further more preferably 3,500,000 or more, still further more preferably 4,000,000 or more.

Further, in view of productivity, it is preferable that the Mw of a polymer component is adjusted to 8,000,000 or less.

In the flexural strength of the material for a denture base of the first embodiment, in view of further enhancement of the durability (yield point strength) of a denture base formed of this material, the flexural strength of the material for a denture base is preferably 100 MPa or more, more preferably 110 MPa or more, still more preferably 120 MPa or more, even more preferably more than 120 MPa, further more preferably 121 MPa or more.

Meanwhile, although the upper limit of the flexural strength is not particularly limited, in view of cutting workability, the flexural strength is preferably 200 MPa or less.

In the material for a denture base of the first embodiment, in view of impact resistance of a denture base formed of this material, the impact strength is preferably 1.41 kJ/m$^2$ or more.

Here, the "impact strength" of a material for a denture base indicates Charpy impact strength measured by Charpy impact test under the condition of edgewise impact in accordance with JIS K7111-1 (2012) when a material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm (the same is applied to the following description).

The impact strength (Charpy impact strength) can be measured using, for example, an impact tester DG-UB equipped with a constant temperature bath manufactured by Toyo Seiki Seisaku-Sho Ltd.

The single-notched test piece can be taken from the material for a denture base of the first embodiment by cutting or the like.

When the impact strength is 1.41 kJ/m$^2$ or more, the impact resistance of a denture base formed of the material for a denture base of the first embodiment is further enhanced.

The impact strength is more preferably 2.0 kJ/m$^2$ or more.

Although the upper limit of the impact strength is not particularly limited, the upper limit may be 11.0 kJ/m$^2$, for example. The upper limit of the impact strength may be 6.0 kJ/m$^2$ or 4.0 kJ/m$^2$.

In the material for a denture base of the first embodiment, the flexural modulus is preferably from 2500 MPa to 3700 MPa, more preferably from 2650 MPa to 3700 MPa, still more preferably from 2700 MPa to 3700 MPa.

Further, the upper limit of the flexural modulus may be 3200 MPa.

Here, the "flexural modulus" indicates a flexural modulus measured by a three-point flexural test under the same conditions as the above-described "flexural strength". The flexural modulus is calculated by a "secant method".

<Polymer Component>

The polymer component in the first embodiment contains an acrylic resin and has a weight average molecular weight (Mw) of 1,200,000 or more.

The Mw referred to herein means the Mw of the (entire) polymer component.

Needless to say, when the polymer component is formed only of the acrylic resin, the Mw of the polymer component matches the Mw of the acrylic resin.

The preferable ranges of the Mw of the polymer component are as described above.

In the polymer in the first embodiment, the molecular weight distribution (Mw/Mn) is preferably from 1.1 to 20, more preferably from 1.1 to 15, still more preferably from 1.1 to 10, even more preferably from 1.1 to 7.0, further more preferably from 1.5 to 6.0, particularly preferably from 2.0 to 5.5.

In this specification, the weight average molecular weight (Mw) and the molecular weight distribution (Mw/Mn) indicate respective values measured using a gel permeation chromatograph (GPC) by the following GPC measuring method.

—GPC Measuring Apparatus—
LC-10AD manufactured by Shimadzu Corporation
—Column—
Shodex K-806L 30 cm×2
—Preparation of Sample—

A polymer component to be measured is dissolved in a solvent (tetrahydrofuran) at room temperature (20° C. to 30° C.) to prepare a sample solution having a concentration of 0.1% (w/v).

—Measurement Conditions—

100 μL of the sample solution is introduced into the column at a column temperature of 40° C. and a flow rate of 1.0 mL/min. with a mobile phase (for example, tetrahydrofuran).

The sample concentration in the sample solution separated in the column is measured with a differential refractometer (RI-101). A universal calibration curve is created with a polymethylmethacrylate standard sample, and the weight average molecular weight (Mw), a number average molecular weight (Mn), and the molecular weight distribution (Mw/Mn) of the polymer component are calculated.

Analysis can be performed using data processing software Empower 2 (manufactured by Waters Corporation), for example.

From the standpoint of ease of realization of the fact that the weight average molecular weight (Mw) of the polymer component is 1,200,000 or more, as the acrylic resin contained in the polymer component, an acrylic resin obtained by polymerizing a monomer, an acrylic resin obtained by polymerizing an oligomer or a prepolymer, or an acrylic resin obtained by polymerizing a mixture of an oligomer or a prepolymer and a monomer is preferably used. As the oligomer or the prepolymer, an oligomer or a prepolymer having fluidity at room temperature is particularly preferably used.

A usual acrylic resin for dentures is an acrylic resin obtained by polymerizing a mixture of a polymer in a solid state at room temperature and a monomer.

However, when as the acrylic resin in the first embodiment, the acrylic resin obtained by polymerizing the mixture of a polymer in a solid state at room temperature and a monomer is used, there is a tendency that it is difficult that the Mw of the polymer component containing the acrylic resin is 1,200,000 or more (preferably 1,500,000 or more).

For example, a denture base formed of the usual acrylic resin for dentures is manufactured by mixing an acrylic polymer, which is a powder in a solid state at room temperature and has a relatively high molecular weight, a monomer for an acrylic compound, and a polymerization initiator, polymerizing the mixture to a state with fluidity, then pouring the polymerized mixture into a gypsum mold or the like, and curing the mixture by heating or the like. This method of manufacturing a denture base is usually performed by a dental technician, and since the polymerization rate is high, the method has an advantage that it is convenient for the dental technician. However, in this method, since a difference in molecular weight between a powder as a starting raw material and a monomer is large, it is assumed that the Mw of the acrylic resin is hardly increased.

With respect to the above usual method, for example, only an oligomer or a prepolymer having fluidity at room temperature, or a mixture obtained by adding a monomer to an oligomer or a prepolymer is polymerized over several days to several weeks near the polymerization temperature of the oligomer or the prepolymer, such that a degree of polymerization and uniformity of polymerization can be enhanced. Consequently, it is considered that the Mw of the acrylic resin can be set to 1,200,000 or more, and furthermore, the Mw of the polymer component can be set to 1,200,000 or more.

When the polymer component in the first embodiment contains a rubber, an oligomer or a prepolymer, or a mixture obtained by adding a monomer to an oligomer or a prepolymer is mixed with a rubber, and then the resultant mixture may be polymerized.

(Acrylic Resin)

A polymer component contains an acrylic resin.

Since the material for a denture base in the first embodiment contains a highly transparent acrylic resin, the material has an advantage that the degree of freedom of coloring is high. Further, since the material for a denture base in the first embodiment contains an acrylic resin, the material has an advantage that the adhesiveness to a commercially available acrylic artificial tooth is excellent.

The polymer component in the first embodiment may contain only one kind or two or more kinds of acrylic resin.

In this specification, an acrylic resin indicates a polymer containing at least one structural unit selected from the group consisting of a structural unit derived from acrylic acid, a structural unit derived from methacrylic acid, a structural unit derived from acrylic acid ester, and a structural unit derived from methacrylic acid ester.

Namely, the acrylic resin in this specification is a polymer obtained by polymerizing a monomer component containing at least one kind (hereinafter also referred to as an "acrylic monomer") selected from the group consisting of acrylic acid, methacrylic acid, acrylic acid ester, and methacrylic acid ester.

An acrylic monomer as at least a portion of a raw material of an acrylic resin may be a monofunctional acrylic monomer or a polyfunctional acrylic monomer.

Examples of the monofunctional acrylic monomer include acrylic acid, methacrylic acid, acrylic acid ester containing one acryloyl group in a molecule, and methacrylic acid ester containing one methacryloyl group in a molecule.

Examples of the polyfunctional acrylic monomer include acrylic acid ester containing two or more acryloyl groups in a molecule and methacrylic acid ester containing two or more methacryloyl groups in a molecule.

More specific examples of the acrylic resin include a homopolymer of acrylic acid, a homopolymer of methacrylic acid, a homopolymer of acrylic acid ester, a homopolymer of methacrylic acid ester, a copolymer of acrylic acid and another monomer (for example, acrylic acid ester, methacrylic acid, methacrylic acid ester, or α-olefin (for example, ethylene)), a copolymer of methacrylic acid and another monomer (for example, acrylic acid, acrylic acid ester, methacrylic acid ester, or α-olefin (for example, ethylene)), a copolymer of acrylic acid ester and another monomer (for example, acrylic acid, methacrylic acid, methacrylic acid ester, or α-olefin (for example, ethylene)), and a copolymer of methacrylic acid ester and another monomer (for example, acrylic acid, acrylic acid ester, methacrylic acid, or α-olefin (for example, ethylene)).

The acrylic acid ester is preferably an acrylic acid alkyl ester, more preferably a linear alkyl ester or branched-chain alkyl ester of acrylic acid, and still more preferably the linear alkyl ester of acrylic acid.

Further, it is preferable that the acrylic acid ester contains no halogen atom such as fluorine atoms and chlorine atoms.

The acrylic acid ester is more preferably an acrylic acid alkyl ester in which the number of carbons of an alkyl group contained at an alkyl ester is 1 to 4, still more preferably methyl acrylate or ethyl acrylate, and particularly preferably methyl acrylate.

The methacrylic acid ester is preferably a methacrylic acid alkyl ester, more preferably a linear alkyl ester or branched-chain alkyl ester of methacrylic acid, and still more preferably the linear alkyl ester of methacrylic acid.

Further, it is preferable that the methacrylic acid ester contains no halogen atom such as fluorine atoms and chlorine atoms.

The methacrylic acid ester is more preferably a methacrylic acid alkyl ester in which the number of carbons of an alkyl group contained at an alkyl ester is 1 to 4, still more preferably methyl methacrylate or ethyl methacrylate, and particularly preferably methyl methacrylate.

In view of reactivity and productivity, the acrylic resin is preferably a polymer obtained by polymerizing a monomer component containing a monofunctional acrylic monomer.

The acrylic resin is more preferably a polymer obtained by polymerizing a monomer component containing 50% by mass or more (preferably 80% by mass or more, still more preferably 90% by mass or more, even more preferably 95% by mass or more) of a monofunctional acrylic monomer.

The monofunctional acrylic monomer is preferably at least one kind selected from the group consisting of acrylic acid, methacrylic acid, acrylic acid alkyl ester, and methacrylic acid alkyl ester.

In view of physical properties (heat resistance) of a material for a denture base and a denture base, the monofunctional acrylic monomer is more preferably at least one kind selected from the group consisting of a methacrylic acid and a methacrylic acid alkyl ester.

The respective preferable ranges of the acrylic acid alkyl ester and the methacrylic acid alkyl ester are the same as described above.

As preferred embodiments of the acrylic resin, an embodiment in which the monofunctional acrylic monomer is a methacrylic acid alkyl ester is exemplified. Hereinafter, the acrylic resin according to this embodiment is also referred to as an "acrylic resin X".

The acrylic resin X is preferably a polymer obtained by polymerizing a monomer component containing methyl methacrylate (namely, this polymer is a polymer containing a structural unit derived from methyl methacrylate) and particularly preferably a homopolymer of methyl methacrylate (polymethyl methacrylate, that is, polymethylmethacrylate (PMMA)).

As another preferred embodiment of the acrylic resin, there is exemplified an embodiment in which the monofunctional acrylic monomer consists of methacrylic acid and methacrylic acid alkyl ester, and an amount of methacrylic acid based on the total amount of methacrylic acid methacrylic acid alkyl ester is more than 0% by mass and 15% by mass or less (more preferably from 0.1% by mass to 15% by mass, still more preferably from 1% by mass to 15% by mass, even more preferably from 5% by mass to 15% by mass). Hereinafter, the acrylic resin according to this embodiment is also referred to as an "acrylic resin Y".

As compared to the acrylic resin X (for example, PMMA), the acrylic resin Y is advantageous in terms of the flexural strength of a material for a denture base and durability (yield point strength in a compression test) of a denture base.

As the acrylic resin Y, a methacrylic acid alkyl ester-methacrylic acid copolymer in which the content of the structural unit derived from methacrylic acid is 15% by mass or less is particularly preferably used.

The polymer component in the first embodiment may contain only one kind of acrylic resin or may contain two or more kinds of acrylic resin.

Further, the polymer component in the first embodiment may contain a resin other than the acrylic resin.

Incidentally, the content of the acrylic resin in the material for a denture base in the first embodiment (when two or more kinds of acrylic resin are used, the content is a total content) based on the total amount of the material for a denture base is preferably 60% by mass or more, more preferably 80% by mass or more, still more preferably 90% by mass or more, even more preferably 95% by mass or more, particularly preferably 99% by mass or more.

(Rubber)

The polymer component in the first embodiment may contain a rubber.

When the polymer component in the first embodiment contains a rubber, the impact strength of the material for a denture base is further enhanced, and the impact resistance of a denture base formed of this material is further enhanced.

Examples of the kind of rubber include acrylic rubber, butadiene rubber, butadiene-acrylic rubber, butadiene-styrene rubber, and silicone rubber.

When the polymer component in the first embodiment contains a rubber, the kind of rubber may be suitably selected in consideration of physical properties. Considering a balance among various properties such as hardness and impact resistance, butadiene rubber or butadiene-acrylic rubber is preferably used.

When the polymer component in the first embodiment contains a rubber, only one kind of rubber or two or more kinds of rubbers may be contained in the polymer component.

It is preferable that the rubber contains a polymer obtained by graft polymerization of a rubbery polymer (preferably a rubbery polymer having a cross-linked structure) with a thermoplastic resin component.

The thermoplastic resin component is not particularly limited as long as it is a monomer component capable of graft polymerizing with a rubbery polymer. Examples of the thermoplastic resin component include an aromatic vinyl compound, a vinyl cyanide compound, a (meth)acrylic acid ester compound, a (meth)acrylic acid compound, an N-substituted maleimide compound, an $\alpha,\beta$-unsaturated carboxylic acid compound, and anhydrides thereof (for example, maleic anhydride, etc.). These monomer components may be used in one kind alone, or in two or more kinds in combination.

Here, "(meth)acrylic acid" is a concept including both acrylic acid and methacrylic acid (the same is applied to the following description).

Examples of the rubbery polymer include an acrylic (co)polymer, a butadiene (co)polymer, and a silicone-based polymer. Among them, a butadiene (co)polymer is preferably used. When the rubbery component is a butadiene (co)polymer, the impact strength of the material for a denture base is further enhanced, and the impact resistance of the denture base formed of this material is further enhanced.

Here, "(co)polymer" is a concept including both a homopolymer and a copolymer (the same is applied to the following description).

As the acrylic (co)polymer, a copolymer obtained by polymerizing a mixture of one or more kinds of acrylic acid alkyl esters in which the number of carbons of the alkyl group is from 2 to 8 and one or more kinds of polyfunctional monomers is preferably used.

The mixture may contain, if necessary, a copolymerizable monomer such as styrene; a styrene derivative such as α-methyl styrene and vinyl toluene; acrylonitrile; and methyl methacrylate (styrene or a mixture of styrene and a styrene derivative is preferably contained).

Examples of the acrylic acid alkyl ester in which the number of carbons of the alkyl group is from 2 to 8 include ethyl acrylate, n-butyl acrylate, and 2-ethylhexyl acrylate. Among them, n-butyl acrylate is more preferably used.

Examples of a polyfunctional monomer include a well-known acrylic polyfunctional monomer and a well-known polyvalent aromatic vinyl monomer (for example, divinylbenzene).

The amount of a component constituting the acrylic (co)polymer is not particularly limited. The acrylic (co) polymer is preferably a copolymer obtained by copolymerizing 50.0% by mass to 99.9% by mass of an acrylic acid alkyl ester, 0.1% by mass to 10% by mass of a polyfunctional monomer, and 0% by mass to 49.9% by mass of a copolymerizable monomer.

The rubber obtained by graft polymerization of an acrylic (co)polymer with a thermoplastic resin component is commercially available, and examples thereof include "Metablen (trademark) W-450" manufactured by Mitsubishi Rayon Co., Ltd.

Examples of a butadiene (co)polymer include a butadiene-n-butyl acrylate copolymer and a butadiene-styrene copolymer.

The butadiene (co)polymer is preferably a copolymer obtained by copolymerizing 5% by mass or more of 1,3-butadiene and 95% by mass or less of at least one kind of monomer that is copolymerizable with 1,3-butadiene.

Examples of the monomer that is copolymerizable with 1,3-butadiene include styrene, acrylonitrile, and the above-described acrylic acid alkyl ester in which the number of carbons of the alkyl group is from 2 to 8.

In the copolymerization of the monomer that is copolymerizable with 1,3-butadiene, with 1,3-butadiene, a polyfunctional monomer may be used together.

Here, examples of the polyfunctional monomer include a well-known acrylic polyfunctional monomer and a well-known polyvalent aromatic vinyl monomer (for example, divinylbenzene).

In terms of further enhancement of the impact strength of the material for a denture base and further enhancement of the impact resistance of an obtained denture base, a butadiene (co)polymer is preferably a butadiene-n-butyl acrylate copolymer obtained by copolymerizing butadiene and n-butyl acrylate.

The rubber obtained by graft polymerization of a butadiene (co)polymer with a thermoplastic resin component is commercially available, and examples thereof include "MUX-60" manufactured by UMG ABS, Ltd. and "KANE ACE (trademark) M-521" manufactured by Kaneka Corporation.

Examples of a silicone-based polymer include room temperature curable silicone rubber and thermosetting silicone rubber. Specific examples of the silicone-based polymer include dimethyl silicone rubber, vinylmethyl silicone rubber, methylphenyl silicone rubber, and fluorosilicone rubber. As the silicone-based polymer, well-known silicone rubber may be used.

The rubber obtained by graft polymerization of a silicone-based polymer with a thermoplastic resin component is commercially available, and examples thereof include "Metablen (trademark) S-2001" manufactured by Mitsubishi Rayon Co., Ltd.

The rubber is preferably rubber particles.

When the polymer component in the first embodiment contains rubber particles as a rubber, the rubber particles are dispersed in an acrylic resin. Therefore, the impact strength of the material for a denture base is further enhanced.

Examples of rubber particles include rubber particles having a monolayer structure and rubber particles having a multilayer structure.

The rubber particles having a multilayer structure may be provided with, for example, an inner layer of a rubbery polymer, such as the above-described acrylic (co)polymer, the above-described butadiene (co)polymer, and the above-described silicone-based polymer, and an outer layer of a resin obtained by polymerizing the above-described thermoplastic resin component around the inner layer.

Meanwhile, a rubber in which a small amount of cross-linkable polyfunctional monomer is copolymerized with a rubbery polymer may be used.

As the resin obtained by polymerizing a thermoplastic resin component, a polymer whose glass transition temperature is higher than room temperature is preferably used.

For example, acrylic rubber particles may have a monolayer structure of a rubbery polymer mainly composed of methyl methacrylate or a multilayer structure in which a thermoplastic resin layer mainly composed of methyl methacrylate is provided around an inner layer which is an elastic resin layer mainly composed of acrylic acid alkyl ester such as n-butyl acrylate, or well-known acrylic rubber particles may be used.

The rubber particles are more preferably rubber particles obtained by graft polymerization of a rubbery polymer (preferably a rubbery polymer having a cross-linked structure) with a thermoplastic resin component.

As described above, examples of the rubbery polymer include an acrylic (co)polymer, a butadiene (co)polymer, and a silicone-based polymer. Among them, the butadiene (co)polymer is preferably used.

The average particle diameter of rubber particles is preferably in a range of from 0.03 µm to 2.0 µm. Consequently, a dispersion state of the rubber particles in the material for a denture base can be suitably maintained. The rubber particles having such a particle diameter can be produced by an emulsion polymerization method.

When the polymer component in the first embodiment contains a rubber, the content of the rubber based on the total amount of the material for a denture base is preferably from 1% by mass to 10% by mass.

When the content of the rubber is 1% by mass or more, the impact strength of the material for a denture base is further enhanced, and the impact resistance of a denture base formed of this material is further enhanced.

When the content of the rubber is 10% by mass or less, the flexural strength of the material for a denture base is further enhanced, and the durability (yield point strength in a compression test) of a denture base formed of this material is further enhanced. Further, when the content of the rubber is 10% by mass or less, the flexural modulus of the material for a denture base is further enhanced. Therefore, the material for a denture base is less likely to be deformed, so that workability in manufacturing a denture base is further enhanced.

The upper limit of the content of the rubber is preferably 8% by mass, more preferably 7% by mass.

The lower limit of the content of the rubber is preferably 1.5% by mass, more preferably 2% by mass, particularly preferably 3% by mass.

<Other Components>

The material for a denture base in the first embodiment may contain other components, if necessary.

Examples of other components include a colorant.

The colorant is not particularly limited, and pigments, dyes, colored fibers, or the like may be used. Among them, pigments and dyes are preferably used, and pigments are particularly preferably used.

When the material for a denture base in the first embodiment contains a colorant, the content of the colorant based on 100 parts by mass of the polymer is preferably from 0.001 parts by mass to 0.20 parts by mass, more preferably from 0.001 parts by mass to 0.15 parts by mass, still more preferably from 0.001 parts by mass to 0.10 parts by mass.

When the content of the colorant is 0.20 parts by mass or less, the flexural strength of the material for a denture base of 100 MPa or more is more easily achieved.

The material for a denture base in the first embodiment may contain a material simulating a blood vessel, and the content of the material having a minor axis of 20 µm or more, based on 100 parts by mass of the polymer, is preferably less than 0.001 parts by mass, more preferably less than 0.0005 parts by mass. When the content of the material having a minor axis of 20 µm or more is adjusted within the above range, the flexural strength is likely to be adjusted to 100 MPa or more.

When the material is fibrous, the minor axis is the average diameter of fibers.

The denture base of the present invention may be obtained in the following manner that an uncolored material for a denture base as the material for a denture base in the first embodiment is cut to obtain an uncolored denture base, and after that, the uncolored denture base is colored with a colorant. In this case, the material for a denture base in the first embodiment does not necessarily contain a colorant.

In the material for a denture base in the first embodiment, each content of inorganic fibers and inorganic whiskers based on the total amount of the material for a denture base is preferably 0.5% by mass or less, more preferably 0.1% by mass or less, particularly preferably 0% by mass (namely, the material for a denture base in the first embodiment contains no inorganic fiber and inorganic whisker).

Here, the fact that "each content of inorganic fibers and inorganic whiskers based on the total amount of the material for a denture base is preferably 0.5% by mass or less" means that the material for a denture base in the first embodiment substantially does not contain inorganic fibers and inorganic whiskers. In this case, since a denture base to be manufactured also contains no inorganic fiber and inorganic whisker, the effect of obtaining extremely smooth surface of the denture base in a microscopic view point and the effect of accordingly obtaining extremely good wearing feeling of the denture base are expected.

In the material for a denture base in the first embodiment, the content of the polymer component based on the total amount of the material for a denture base is preferably 90% by mass or more, more preferably 95% by mass or more, particularly preferably 99% by mass or more.

When the content of the polymer component is 90% by mass or more, the flexural strength of the material for a denture base is further enhanced.

The material for a denture base in the first embodiment is preferably a material for a denture base used in manufacturing a denture base by cutting.

In this case, the material for a denture base in the first embodiment is preferably a block body having a thickness of from 10 mm to 40 mm in view of ease of manufacturing the material for a denture base (ease of polymerizing a raw material) and reducing the amount of wasted portions in cutting out a denture base. The thickness of the block body is more preferably from 20 mm to 40 mm.

The size of the block body is not particularly limited as long as it is capable of obtaining a denture base by cutting.

Also, although the shape of the block body is not particularly limited, in view of ease of fixing the block body to a cutting machine, the block body preferably has a three-dimensional shape having an upper surface and a lower surface (that is, two surfaces facing each other). The block body more preferably has a rectangular solid shape in view of ease of creating a cutting program and still more preferably has a large rectangular solid shape capable of cutting a plurality of block bodies at once.

For example, when a block body in an after-mentioned embodiment having a rectangular solid shape having a size of 230 mm×190 mm×30 mm is used, four full removable denture bases can be obtained at once, and thus it is efficient.

Although a method of manufacturing the material for a denture base in the first embodiment is not particularly limited, it is preferable to use an oligomer or to use a prepolymer or to use a mixture of an oligomer or a prepolymer and a monomer, as a raw material, and slowly polymerize the material over about several days to one week near the polymerization temperature. According to this manufacturing method, a material for a denture base containing a polymer component having a Mw of 1,200,000 or more and containing an acrylic resin is likely to be manufactured.

When the material for a denture base in the first embodiment contains a rubber, preferably, an oligomer or a prepolymer or a mixture obtained by adding a monomer to an oligomer or a prepolymer is mixed with rubber to obtain a raw material, and then the raw material is slowly polymerized over about several days to one week near the polymerization temperature to manufacture the material for a denture base.

The raw material may contain other components (such as a colorant and an initiator), if necessary.

Next, a preferred embodiment of the material for a denture base in the first embodiment will be described.

Incidentally, the following embodiments may partially overlap with each other.

<Embodiment A>

A material for a denture base in the embodiment A is a material for a denture base which contains a polymer component having a Mw of 1,500,000 or more and containing an acrylic resin, and the has flexural strength of 110 MPa or more.

The embodiment A focuses on the flexural strength of the material for a denture base, and according to the material for a denture base in the embodiment A, a denture base which is excellent particularly in durability can be manufactured.

More preferable ranges of the material for a denture base in the embodiment A are as already described as preferable ranges of the material for a denture base in the first embodiment, except for the content of a rubber (see below).

In the material for a denture base in the embodiment A, the content of a rubber based on the total amount of the material for a denture base is more preferably less than 1% by mass, particularly preferably 0% by mass (namely, the material for a denture base contains no rubber).

<Embodiment B>

A material for a denture base in the embodiment B is a material for a denture base which contains a polymer component having a Mw of 1,500,000 or more and containing an acrylic resin, and has impact strength of 2.0 kJ/m$^2$ or more and flexural strength of 100 MPa or more.

The embodiment B focuses on the balance between the flexural strength of the material for a denture base and the impact strength of the material for a denture base, and according to the material for a denture base in the embodiment B, a denture base which is excellent particularly in a balance between durability and impact resistance can be manufactured.

The polymer component in the embodiment B preferably contains a rubber in view of the impact strength.

The kind of a rubber and a preferable range of the content in the embodiment B are as already described as the kind of rubber and the preferable range of the content in the first embodiment.

The flexural strength of the material for a denture base in the embodiment B is preferably 200 MPa or less in view of further enhancement of the impact strength. The flexural strength of the material for a denture base in the embodiment B is preferably 150 MPa or less, more preferably 120 MPa or less, still more preferably less than 110 MPa.

Preferable ranges of the material for a denture base in the embodiment B are as already described as preferable ranges of the material for a denture base in the first embodiment.

<Embodiment C>

A material for a denture base in the embodiment C contains a polymer component having a Mw of 1,200,000 or more and containing the above-described acrylic resin Y, and has flexural strength of 110 MPa or more.

The acrylic resin Y is preferably a methacrylic acid alkyl ester-methacrylic acid copolymer in which the content of a structural unit derived from methacrylic acid is 15% by mass or less.

The embodiment C focuses on the flexural strength of the material for a denture base, and according to the material for a denture base in the embodiment C, a denture base which is excellent particularly in durability can be manufactured.

The polymer component in the embodiment C may contain a rubber.

When a rubber is contained in the embodiment C, the rubber and a preferable range of the content thereof are as already described as the rubber and the preferable range of the content thereof in the first embodiment.

In the material for a denture base according to the embodiment C, the content of the rubber based on the total amount of the material for a denture base may be less than 1% by mass or 0% by mass (namely, the material for a denture base may not contain a rubber).

Other preferable ranges of the material for a denture base according to the embodiment C are as already described as the preferable ranges of the material for a denture base in the first embodiment.

<Second Embodiment>

A material for a denture base in the second embodiment has flexural strength of 110 MPa or more and contains a polymer component that is at least one kind selected from the group consisting of a sulfone-based resin and an ether ketone resin.

The "flexural strength" in the second embodiment is synonymous with the "flexural strength in a three-point flexural test" in the first embodiment.

According to the material for a denture base in the second embodiment, there is provided an effect similar to that in the material for a denture base in the first embodiment, that is, the effect of enhancing the durability (enhancing the yield point strength in a compression test) of a denture base formed of this material.

Further, according to the material for a denture base in the second embodiment, the impact strength of the material for a denture base and the impact resistance of a denture base formed of this material are further enhanced.

In the material for a denture base in the second embodiment, in view of further enhancement of the durability (yield point strength) of a denture base formed of this material, the flexural strength is preferably 120 MPa or more, more preferably more than 120 MPa, still more preferably 121 MPa or more.

Meanwhile, although the upper limit of the flexural strength is not particularly limited, in view of cutting workability, the flexural strength is preferably 200 MPa or less.

In the material for a denture base in the second embodiment, the impact strength is preferably 1.41 kJ/m$^2$ or more.

When the impact strength of the material for a denture base in the second embodiment is 1.41 kJ/m$^2$ or more, the impact resistance of a denture base formed of this material is further enhanced.

The "impact strength" in the second embodiment is synonymous with the "impact strength" in the first embodiment.

A preferable range of the impact strength of the material for a denture base in the second embodiment is similar to the impact strength of the material for a denture base in the second embodiment.

However, the impact strength of the material for a denture base in the second embodiment may be 2.0 kJ/m$^2$ or more, 3.0 kJ/m$^2$ or more, or 3.5 kJ/m$^2$ or more.

In the material for a denture base in the second embodiment containing a sulfone-based resin, since the sulfone-based resin is highly transparent, the material has an advantage that the degree of freedom of coloring is high. In this case, only one kind or two or more kinds of sulfone-based resins may be contained in the material.

Here, the sulfone-based resin indicates a polymer containing a structural unit having a sulfonyl group (—SO$_2$— group) and is preferably a polymer containing a structural unit having a sulfonyl group (—SO$_2$— group) and a phenylene group.

More specific examples of the sulfone-based resin include polysulfone (PSU), polyether sulfone (PES), and polyphenyl sulfone (PPSU), and polysulfone (PSU) or polyphenyl sulfone (PPSU) is preferably used.

In view of the impact strength of the material for a denture base (that is, the impact resistance of a denture base formed of this material), polyphenyl sulfone (PPSU) is particularly preferably used.

The material for a denture base in the second embodiment containing an ether ketone-based resin has an advantage that the flexural strength is particularly high. In this case, only one kind or two or more kinds of ether ketone-based resins may be contained in the material.

Here, the ether ketone-based resin indicates a polymer containing a structural unit having an ether group (—O— group) and a ketone group (—C(=O)— group) and is preferably a polymer containing a structural unit having an ether group (—O— group), a phenylene group, and a ketone group (—C(=O)— group).

More specific examples of the ether ketone-based resin include a polyether ether ketone (PEEK) resin, a polyether ketone (PEK) resin, a polyether ketone ketone (PEKK) resin, a polyether ether ketone ketone (PEEKK) resin, and a polyether ketone ether ketone ketone (PEKEKK) resin, and polyether ether ketone (PEEK) is particularly preferably used.

In view of the impact strength of the material for a denture base (that is, the impact resistance of a denture base formed of this material), the polymer component in the second embodiment is particularly preferably at least one kind selected from the group consisting of polyphenyl sulfone and polyether ether ketone.

Other preferable ranges of the material for a denture base in the second embodiment are similar to preferable ranges of the material for a denture base in the first embodiment.

[Denture Base, Plate Denture]

The denture base of the present invention contains the material for a denture base of the invention.

Here, the "material for a denture base of the invention" means the material for a denture base in the first embodiment or the second embodiment (the same is applied to the following description).

Accordingly, the denture base of the invention is excellent in durability (yield point strength).

The denture base of the present invention may be a denture base for full removable denture (so-called full denture) or a denture base for partial removable denture (so-called partial denture).

Further, the denture base of the invention may be a denture base for maxillary denture (hereinafter also referred to as a "maxillary denture base"), a denture base for submaxillary denture (hereinafter also referred to as a "submaxillary denture base"), or a set of the maxillary denture base and the submaxillary denture base.

In the denture base of the present invention, only a portion of the denture base may be formed of the material for a denture base of the invention, or the entire denture base may be formed of the material for a denture base of the invention.

Examples of the denture base in which only a portion thereof is formed of the material for a denture base of the invention include a denture base in which at least a portion of a resin portion of the denture base (so-called metal base) including a metal portion and the resin portion is formed of the material for a denture base of the invention and a denture base in which only a portion of the denture base (so-called resin base) including only a resin portion is formed of the material for a denture base of the invention.

Examples of the denture base entirely formed of the material for a denture base of the invention include a denture base including only a resin portion.

The denture base of the present invention is particularly preferably a denture base obtained by cutting a material for a denture base, which is a block body having a thickness of from 10 mm to 40 mm, as a preferred embodiment of the material for a denture base of the invention.

The plate denture of the present invention contains the denture base of the invention and artificial teeth fixed to the denture base.

Accordingly, the plate denture of the invention is excellent in the durability (yield point strength) of the denture base.

The plate denture of the invention may be a partial removable denture or a full removable denture. Namely, the plate denture of the invention has only to contain at least one artificial tooth.

Further, the plate denture of the invention may be a maxillary denture, a submaxillary denture, or a set of the maxillary denture and the submaxillary denture.

The artificial tooth may be formed of an acrylic resin, for example. Examples of the acrylic resin are the same as described above. The artificial tooth may further contain a filler and the like in addition to the acrylic resin.

FIG. 1 is a perspective view conceptually showing an example of the plate denture of the present invention.

As shown in FIG. 1, a maxillary denture 10 as an example of the plate denture of the invention is provided with a maxillary denture base 20 as an example of the denture base of the invention, an artificial tooth 12 fixed to the maxillary denture base 20. In FIG. 1, only one of artificial teeth is denoted with the reference numeral 12.

The maxillary denture base 20 is manufactured by cutting the material for a denture base of the invention. The maxillary denture 10 is manufactured by fixing the artificial tooth 12 to the maxillary denture base 20.

Although illustration is omitted, the denture base is separated into a plurality of portions, and only a portion thereof may be manufactured by cutting the material for a denture base of the present invention.

The denture base and the plate denture of the invention are not limited to a denture base for maxillary denture and a plate denture for maxillary denture, respectively, and they may be naturally a denture base for submaxillary denture and a plate denture for submaxillary denture, respectively.

[Method of Manufacturing Denture Base, Method of Manufacturing Plate Denture]

The method of manufacturing a denture base of the present invention includes a cutting process of cutting a material for a denture base, which is a block body having a thickness of from 10 mm to 40 mm, as a preferred embodiment of the material for a denture base of the invention and thus obtaining a denture base.

In the cutting process, it is preferable to cut the material for a denture base which is the block body with the use of a CAD (Computer Aided Design)/CAM (Computer Aided Manufacturing) system to obtain a denture base.

Cutting using the CAD/CAM system can be performed using a CNC (Computer Numerical Control) cutting machine in accordance with a cutting program created by CAD/CAM software.

The cutting program can be created by a well-known method based on a three-dimensional shape inside an oral cavity of a patient. When a denture base suitable for a patient has been already manufactured, the denture base is optically scanned to obtain three-dimensional (3D) data, and a cutting program may be created based on the obtained 3D data.

In view of cutting a plurality of materials for a denture base at once, it is preferable that a changer device which can automatically exchange the material for a denture base is provided adjacent to the CNC cutting machine.

The method of manufacturing a denture base of the present invention may include processes other than the cutting process, if necessary. Examples of other processes include a coloring process of coloring the denture base.

The method of manufacturing a plate denture of the present invention includes a cutting process of cutting the material for a denture base of the invention to obtain a denture base and a fixing process of fixing an artificial tooth to the denture base.

The preferred embodiment of the cutting process is as described above.

In the fixing process, an artificial tooth can be fixed by a usual method using an adhesive. As the adhesive, a dental adhesive resin cement "Super-Bond" (trademark) manufactured by Sun Medical Co., Ltd. may be used, for example.

Before an artificial tooth is fixed to a denture base with the use of an adhesive, well-known surface treatment (easy adhesion treatment) may be previously applied to a surface (adhesion surface) of at least one of the denture base and the artificial tooth.

The method of manufacturing a plate denture of the present invention may include processes other than the cutting process and the fixing process, if necessary. Examples of other processes include a coloring process of coloring a denture base of the plate denture.

EXAMPLES

Hereinafter, although the embodiments of the present invention will be more specifically described using examples, they are not limited to the following examples unless they deviate from the spirit thereof.

Hereinafter, "wt %" is synonymous with % by mass.

Further, hereinafter, Examples 1A to 3A are examples of the material for a denture base in the embodiment A in the first embodiment, Examples 1B to 6B are examples of the material for a denture base in the embodiment B in the first embodiment, Example 1C is an example of the material for a denture base in the embodiment C in the first embodiment, and Examples 1D to 3D are examples of the material for a denture base in the second embodiment.

Example 1A

<Preparation of Test Piece for Flexural Test>

As the material for a denture base in the embodiment A in the first embodiment, a resin block ("Kanase Lite" manufactured by Kanase Industries, Co., Ltd.; the material was polymethylmethacrylate (PMMA); the shape iss a rectangular solid shape having a size of 230 mm×190 mm×30 mm) was provided, and the resin block was cut to obtain a rectangular solid-shaped test piece for flexural test having a size of 80 mm×10 mm×4 mm.

<Three-Point Flexural Test (Measurement of Flexural Strength and Flexural Modulus)>

The three-point test of the test piece for flexural test was conducted in accordance with JIS K7171 (2008) with the use of a 5-hook flexural test machine model 2001-5 manufactured by Intesco Co., Ltd. to measure the flexural strength and the flexural modulus.

Here, the testing speed was 2 mm/min, and a length of the support span was 64 mm. The flexural modulus was calculated by a secant method The result is shown in the following Table 1.

<Preparation of Test Piece for Impact Test>

A resin piece having the same size as the test piece for flexural test was prepared by a similar method, and the resin piece was allowed to have a notch having the shape A prescribed by JIS K7111-1 (2012) such that a remaining width was 8.0 mm, thus obtaining a test piece for impact test (a single-notched test piece).

<Charpy Impact Test (Measurement of Impact Test)>

The Charpy impact test of the test piece for impact test was conducted under the condition of edgewise impact in accordance with JIS K7111-1 (2012) with the use of an impact tester DG-UB equipped with a constant temperature bath manufactured by Toyo Seiki Seisaku-Sho Ltd., thus measuring the impact strength.

Further, in this test, after a pendulum hit the test piece, the swing angle (°) of the pendulum was measured. The swing angle shows that the smaller the number, the larger energy absorption during hitting, that is, that the impact resistance is excellent.

The above results are shown in the following Table 1.

<Weight Average Molecular Weight (Mw), Number Average Molecular Weight (Mn), and Molecular Weight Distribution (Mw/Mn) of Polymer Component>

In the polymer component (PMMA in Example 1A) in the resin block, the weight average molecular weight (Mw), the number average molecular weight (Mn), and the molecular weight distribution (Mw/Mn) were measured in accordance with the above-described GPC measuring method.

The results are shown in the following Table 1.

<Manufacturing of Denture Base>

3D data of a maxillary denture base manufactured in Comparative Example 1 to be described later was obtained using a 3D scanner.

A cutting program used for cutting the resin block (Kanase Lite) as a material for a denture base to obtain a maxillary denture base was created from the 3D data with the use of CAD/CAM software.

The resin block was cut using a CNC cutting machine in accordance with the cutting program, thus obtaining a maxillary denture base.

<Compression Test of Denture Base (Measurement of Yield Point Strength)>

The compression test (measurement of the yield point strength) of the maxillary denture base was conducted using a universal material testing machine AG-100kNX with a constant temperature bath manufactured by Shimadzu Corporation.

More specifically, the maxillary denture base was placed on a test bed such that a mucosal surface (a surface which is in contact with a residual ridge and a palate portion) was oriented upwardly. Then, a central portion of the maxillary denture base was compressed at a speed of 1 mm/min by a bottom surface of a columnar rod having a diameter of 20 mm (material: carbon steel S45C).

In the compression, displacement and strength were recorded, and a maximum point of the strength was determined as the yield point strength.

The result is shown in the following Table 1.

<Evaluation of Cutting Workability of Material for Denture Base>

In the process from cutting of the resin block as a material for a denture base to acquisition of a denture base, the cutting workability was evaluated based on the following evaluation criteria.

The result is shown in the following Table 1.

—Evaluation Criteria of Cutting Workability—

A: No cracking and chipping occurs during cutting, and the cutting workability was good.
B: At least one of cracking or chipping occurs during cutting, and the cutting workability was bad.

Example 2A

Similar operation to Example 1A was carried out, except that "Kanase Lite" in Example 1A was changed to "CL-000" manufactured by Nitto Jushi Kogyo Co., Ltd. (resin block; the material was PMMA; the shape is a rectangular solid shape having a size of 230 mm×190 mm×30 mm).

The results are shown in the following Table 1.

Example 3A

Similar operation to Example 1A was carried out, except that the test piece for flexural test, the test piece for impact test, and the resin block (Kanase Lite) in Example 1A were changed to a test piece for flexural test, a test piece for impact test, and a resin block produced as follows.

The results are shown in the following Table 1.

<Preparation of Test Piece for Flexural Test (Production Example 1)>

5.09 parts by mass of the A solution (obtained by adding 0.075 parts by mass of a white pigment, 0.013 parts by mass of a red pigment, and 0.002 parts by mass of ARM (2,2'-Azobis (isobutyronitrile); a polymerization initiator) to 5 parts by mass of a methyl methacrylate monomer to mix the mixture under room temperature for homogenization) was added to 95 parts by mass of a preporimerized methyl methacrylate syrup having fluidity at room temperature. The obtained mixture was mixed under room temperature for homogenization and then defoamed. A defoamed composition was poured into a mold in which a gasket was interposed between two inorganic glasses to be polymerized at 40° C. for 48 hours and 120° C. for 5 hours and, thus, to fabricate a rectangular solid-shaped resin block having a thickness of 30 mm.

The resin block was cut to obtain a test piece for flexural test (the material was PMMA) having a size of 80 mm×10 mm×4 mm.

<Preparation of Test Piece for Impact Test>

A resin piece having the same size as the test piece for flexural test obtained as above was prepared by a similar method, and the resin piece was allowed to have a notch having the shape A as in the test piece for impact test in Example 1A and used as a test piece for impact test.

<Fabrication of Resin Block for Manufacturing Denture Base>

A resin block for manufacturing a denture base (having a size of 230 mm×190 mm×30 mm) was fabricated by being cut out from the rectangular solid-shaped resin block fabricated in the preparation of the test piece for flexural test and having a thickness of 30 mm.

Example 1D

Similar operation to Example 1A was carried out, except that "Kanase Lite" in Example 1A was changed to a resin block ("Natural Color" manufactured by Japan Extron Co., Ltd.; the shape is a rectangular solid shape having a thickness of 30 mm) formed of polysulfone (PSU) as the material for a denture base in the second embodiment.

The results are shown in the following Table 1.

Example 2D

Similar operation to Example 1A was carried out, except that "Kanase Lite" in Example 1A was changed to a resin block ("Natural Color" manufactured by Japan Extron Co., Ltd.; the shape is a rectangular solid shape having a thickness of 30 mm) formed of polyether ether ketone (PEEK) as the material for a denture base in the second embodiment.

The results are shown in the following Table 1.

Comparative Example 1

Similar operation to Example 1A was carried out, except that the test piece for flexural test, the test piece for impact test, and the maxillary denture base in Example 1A were changed to a test piece for flexural test, a test piece for impact test, and a maxillary denture base produced as follows.

The results are shown in the following Table 2.

<Preparation of Test Piece for Flexural Test>

(Fabrication of Gypsum Mold for Test Piece for Flexural Test)

First, a flask for manufacturing a denture base (a set of a flask lower mold and a flask upper mold) was provided.

Then, a rectangular solid-shaped board having slightly large length, width, and thickness dimensions as compared to the size of 80 mm (length)×10 mm (width)×4 mm (thickness) was cut out from a resin block. A resin separating agent for a denture base, NEW ACROSEP (manufactured by GC CO., LTD.) was applied onto the entire cut-out board.

Then, the flask lower mold was filled with gypsum dental plaster (manufactured by Noritake Co., Limited) mixed with a predetermined amount of water and then left for a while. After the time when gypsum was partially hardened, a central portion of gypsum was pressed to form a dent having a size large enough to make the board enter the dent.

After the gypsum was completely hardened, dental hard gypsum New Diastone Natural Gray (manufactured by Morita Corporation) mixed with a predetermined amount of water was supplied into the dent and then left for a while. After the time when hard gypsum was partially hardened, the board applied with the separating agent was embedded in the hard gypsum such that only an upper surface of the board was exposed, and a surface of the hard gypsum was smoothed.

After the hard gypsum was completely hardened, the separating agent was applied onto the entire surface of gypsum containing the hard gypsum.

Then, after the flask upper mold was attached above the flask lower mold, the hard gypsum New Diastone Natural Gray mixed with a predetermined amount of water was deposited so as to hide the board.

Then, the gypsum dental plaster mixed with a predetermined amount of water was supplied into a dental flask to the extent that the gypsum dental plaster overflows from the dental flask, and thereafter, the dental flask was lidded. After gypsum was hardened, the flask lower mold and the flask upper mold were separated to remove the board.

According to the above constitution, a gypsum mold for a test piece for flexural test (a set of an upper mold of a gypsum mold and a lower mold of a gypsum mold) was obtained in a flask for manufacturing a denture.

Here, the upper mold of a gypsum mold was fabricated in the flask upper mold, and the lower mold of a gypsum mold was fabricated in the flask lower mold. In the upper mold of a gypsum mold and the lower mold of a gypsum mold, when these two molds are assembled with each other, a space having the shape of the board is formed.

Then, the separating agent was applied onto the entire gypsum surface of the upper mold of a gypsum mold and the lower mold of a gypsum mold.

(Preparation of Test Piece for Flexural test)

MMA was polymerized in a gypsum mold with the use of a flask for manufacturing a denture in which the gypsum mold for a test piece for flexural test was fabricated to obtain a board formed of PMMA and, thus, to polish the obtained board, thereby preparing a test piece for flexural test having a size of 80 mm×10 mm×4 mm. The detailed operation is as follows.

First, a resin material for a denture base, Acron Clear No. 5 (manufacture by GC CO., LTD.) was provided, and 6 g of a powder material and 2.5 g of a liquid material thereof were weighed into a container and then mixed with each other. When the obtained mixture was left for a while to be changed to a rice cake-like state, a generous amount of the rice cake-like mixture was put on a dent of a lower mold of a gypsum mold fabricated in a flask lower mold, and the shape was arranged.

Then, a flask upper mold in which an upper mold of a gypsum mold was fabricated was put on the flask lower mold, and pressure was applied by a pressing machine. Then, the flask upper mold was removed, a rice cake-like resin material for a denture base protruding from the dent was removed. The flask upper mold was put on the flask lower mold again, and pressure was applied by the pressing machine. After that, the flask (in which the flask upper mold and the flask lower mold are assembled with each other) was fixed by a flask clamp.

This flask was put into a pan containing water to be slowly heated to 100° C. for 30 minutes or more by a gas range. The flask was heated for 30 to 40 minutes after reaching 100° C., and then heating was terminated to cool the flask to 30° C.

Subsequently, the flask lower mold and the flask upper mold were separated, and the gypsum mold was then broken to take out a finished board (formed of PMMA). The taken out board was polished to obtain a rectangular solid-shaped board having a size of 80 mm×10 mm×4 mm, and this board was used as a test piece for flexural test (formed of PMMA).

<Preparation of Test Piece for Impact Test>

A resin piece having the same size as the test piece for flexural test obtained as above was prepared by a similar method, and the resin piece was allowed to have a notch having the shape A as in the test piece for impact test in Example 1A and used as a test piece for impact test.

<Manufacturing of Denture Base>

(Manufacturing of Wax Denture)

Primary impressions of the upper jaw and the lower jaw of a patient were taken, and a tray having a shape suitable for the patient was fabricated based on the primary impressions. The precision impression of the patient was taken using the obtained tray. A gypsum model which has a shape suitable for the patient and in which upper and lower portions are separately provided was fabricated based on the taken precision impression.

Then, the upper and lower portions of the gypsum model are combined with each other to fabricate a biteplate used for reproducing occlusion of the upper and lower jaws and formed of a base plate and wax.

Then, a state of jaw movement was observed while watching the oral cavity of the patient, the jaw movement was reproduced by the biteplate to three-dimensionally acquire an occlusion state and, thus, to determine an occlusion position, thereby preparing a wax denture base (a set of a maxillary denture and a submaxillary denture).

Artificial teeth, to that a wax pattern separating agent (manufactured by Shofu Inc.) had been applied in advance, were arranged on the resulted wax denture base, and try-in and adjustment were done to complete a wax denture (a set of a maxillary denture and a submaxillary denture).

(Preparation of Gypsum Mold for Denture Base)

First, a flask for manufacturing a denture constituted of a flask lower mold and a flask upper mold was provided.

Further, artificial teeth were removed from the wax denture to provide a wax denture base.

Then, the wax denture base and the above-described gypsum model were combined with each other, and they were put into the flask lower mold as they were. The flask lower mold was filled with gypsum dental plaster mixed with a predetermined amount of water and then left for a while. After gypsum was hardened, the above-described separating agent was dropped on gypsum to be applied over the entire surface with the use of a brush. After that, the flask upper mold was put on the flask lower mold, and gypsum was supplied therein fully to the frame. The mold was lidded to be left until the gypsum was completely hardened.

After the gypsum was hardened, the flask upper mold and the flask lower mold were separated to be heated with hot water and, thus, to melt out wax, to remove a base plate.

According to the above constitution, a gypsum mold for a denture base constituted of an upper mold of a gypsum mold and a lower mold of a gypsum mold was obtained.

Here, the upper mold of a gypsum mold was fabricated in the flask upper mold, and the lower mold of a gypsum mold was fabricated in the flask lower mold. In the upper mold of a gypsum mold and the lower mold of a gypsum mold, when these two molds are assembled with each other, a space having the shape of the wax denture base is formed.

Then, the separating agent was applied onto the entire gypsum surface of the upper mold of a gypsum mold and the lower mold of a gypsum mold.

(Manufacturing of Denture Base)

In the preparation of a test piece for flexural test in Comparative Example 1, a denture base (a set of a maxillary denture base and a submaxillary denture base; each material was PMMA) was obtained similarly to the preparation of the test piece for flexural test, except that a gypsum mold for a test piece for flexural test was changed to the above-described gypsum mold for a denture base.

Of them, the maxillary denture base was used in a compression test (measurement of the yield point strength), Comparative Examples 2 to 6

Similar operation to Comparative Example 1 was carried out, as shown in the following Table 2, except that Acron Clear No. 5 (manufactured by GC CO., LTD.) in Comparative Example 1 was changed to Acron Live Pink No. 3 (manufactured by GC CO., LTD.), Acron Live Pink No. 8 (manufactured by GC CO., LTD.), Paraexpress Ultra Clear No. 7 (manufactured by Heraeus Kulzer GmbH.), Paraexpress Ultra Pink No. 1 (manufactured by Heraeus Kulzer GmbH.), or Paraexpress Ultra Pink Live No. 34 (manufactured by Heraeus Kulzer GmbH.). In each example, the material for a denture base and the denture base are formed of PMMA.

The results are shown in the following Table 2.

As seen in Table 1 and Table 2, when the flexural strength of the material for a denture base is 100 MPa or more (particularly, 110 MPa or more), the yield point strength in

TABLE 1

| | | | Example 1A | Example 2A | Example 3A | Example 1D | Example 2D |
|---|---|---|---|---|---|---|---|
| Material for denture base | | Material | PMMA | PMMA | PMMA | PSU | PEEK |
| | | Brand or manufacturing method | Kanase Lite | CL-000 | Production Example 1 | Natural Color | Natural Color |
| | Three-point flexural test | Flexural strength [MPa] | 121 | 127 | 124 | 122 | 188 |
| | | Flexural modulus [MPa] | 2941 | 3137 | 3120 | 2533 | 3120 |
| | Charpy impact test | Impact strength [kJ/m$^2$] | 1.41 | 1.47 | 1.52 | 3.25 | 3.5 |
| | | Angle [°] | 132 | 133 | 132 | 118 | 126 |
| | Molecular weight | Mw | 4,550,000 | 4,950,000 | 4,230,000 | N.D. | N.D. |
| | | Mn | 1,150,000 | 1,750,000 | 850,000 | N.D. | N.D. |
| | | Mw/Mn | 4.0 | 2.8 | 5.0 | N.D. | N.D. |
| | | Cutting workability | A | A | A | A | A |
| Method of manufacturing denture base | | | Cutting | Cutting | Cutting | Cutting | Cutting |
| Evaluation of denture base | Compression test | Yield point strength [kN] | 1.5 | 1.8 | 1.9 | 3.0 | 3.9 |

TABLE 2

| | | | Comparative Example 1 | Comparative Example 2 | Comparative Example 3 | Comparative Example 4 | Comparative Example 5 | Comparative Example 6 |
|---|---|---|---|---|---|---|---|---|
| Material for denture base | | Material | PMMA | PMMA | PMMA | PMMA | PMMA | PMMA |
| | | Brand or manufacturing method | Acron clear No. 5 | Acron pink No. 3 | Acron live pink No. 8 | Paraexpress ultra clear No. 7 | Paraexpress ultra pink No. 1 | Paraexpress ultra pink live No. 34 |
| | Three-point flexural test | Flexural strength [MPa] | 99 | 95 | 79 | 83 | 79 | 77 |
| | | Flexural modulus [MPa] | 2858 | 2590 | 2880 | 2900 | 2640 | 2840 |
| | Charpy impact test | Impact strength [kJ/m$^2$] | 1.57 | 1.53 | 1.41 | 1.24 | 1.24 | 1.24 |
| | | Angle [°] | 132 | 133 | 134 | 135 | 135 | 135 |
| | Molecular weight | Mw | 1,150,000 | N.D. | 1,120,000 | 270,000 | N.D. | 260,000 |
| | | Mn | 320,000 | N.D. | 320,000 | 100,000 | N.D. | 100,000 |
| | | Mw/Mn | 3.6 | N.D. | 3.5 | 2.8 | N.D. | 2.6 |
| | | Cutting workability | — | — | — | — | — | — |
| Method of manufacturing denture base | | | Polymerization after putting into mold | | | | | |
| Evaluation of denture base | Compression test | Yield point strength [kN] | 1.1 | 1.0 | 1.0 | 1.1 | 0.9 | 1.1 |

—Description of Table 1 and Table 2—

"N. D." means "No Data" (this similarly applies to Table 3 and subsequent Tables).

"Angle" in the Charpy impact test indicates a swing angle (°) of a pendulum after the pendulum hits a test piece (this similarly applies to Table 3 and subsequent Tables).

As shown in Table 1 and Table 2, the denture bases manufactured by using the materials for a denture base in Examples 1A to 3A corresponding to the material for a denture base in the embodiment A in the first embodiment and the materials for a denture base in Examples 1D and 2D corresponding to the material for a denture base in the second embodiment were all excellent in the durability (yield point strength). In addition, those materials for a denture base were excellent in the cutting workability.

Meanwhile, in the denture bases in Comparative Examples 1 to 6 manufactured by using the material for a denture base in which the Mw of the contained polymer component (PMMA) was less than 120, the durability (yield point strength) was low.

the compression test in a denture base formed of this material is significantly enhanced.

Further, as seen in Table 1, in the material for a denture base in Example 1D, the yield point strength is high although the flexural modulus is 2533 MPa. Meanwhile, as seen in Table 2, in Comparative Examples 1 to 6, the yield point strength is low although the flexural modulus is 2590 MPa or more. These show that even if the flexural modulus is high, there is the case in which the yield point strength of a denture base is low.

Furthermore, in any of the materials for a denture base in Examples 1D and 2D, since the Charpy impact strength is high, it is expected that the impact resistance of denture bases to be obtained is high.

Example 1B

A resin block corresponding to the material for a denture base in the embodiment B of the first embodiment was fabricated. The details are as follows.

First, 2 parts by mass of MUX-60 (manufactured by UMG ABS, Ltd.) as a rubber, 0.002 parts by mass of AIBN(2,2'-Azobis (isobutyronitrile); a polymerization initiator), and 48 parts by mass of methyl methacrylate were mixed under room temperature to obtain a dispersion dispersed with the rubber.

This dispersion was added to 50 parts by mass of a preporimerized methyl methacrylate syrup having fluidity at room temperature and then mixed under room temperature for homogenization.

The homogenized composition was defoamed, and the defoamed composition was poured into a mold in which a gasket is interposed between two inorganic glasses to be polymerized at 40° C. for 48 hours and 120° C. for 5 hours and, thus, to fabricate a rectangular solid-shaped resin block (material for a denture base) having a thickness of 30 mm.

Here, MUX-60 (manufactured by UMG ABS, Ltd.) is a rubber obtained by graft polymerization of a butadiene (co)polymer, which is a rubbery polymer having a cross-linked structure, with a thermoplastic resin component.

Further, the obtained resin block is a resin block formed of a polymer component which is a mixture of PMMA and the rubber (MUX-60).

Similar operation to Example 1A was carried out, except that "Kanase Lite" in Example 1A was changed to the above-described resin block.

The results are shown in the following Table 3.

Example 2B

Similar operation to Example 1B was carried out, except that the amount of MUX-60 (manufactured by UMG ABS, Ltd.) was changed to 4 parts by mass, and the amount of methyl methacrylate was changed to 46 parts by mass.

The results are shown in the following Table 3.

Example 3B

Similar operation to Example 1B was carried out, except that the amount of MUX-60 (manufactured by UMG ABS, Ltd.) was changed to 6 parts by mass, and the amount of methyl methacrylate was changed to 44 parts by mass.

The results are shown in the following Table 3.

corresponding to the embodiment B in the first embodiment were all excellent in the durability (yield point strength) as compared to the above-described denture bases in Comparative Examples 1 to 6 (Table 2). In addition, the materials for a denture base in Examples 1B to 3B were excellent in the cutting workability.

Further, in the materials for a denture base in Examples 1B to 3B, since the Charpy impact strength is high, it is expected that the impact resistance of denture bases to be obtained is high.

Example 1C

A resin block corresponding to the material for a denture base in the embodiment C of the first embodiment was fabricated. The details are as follows.

Similar operation to Production Example 1 in Example 3A was carried out, except that the amount of a methyl methacrylate syrup was changed to 90 parts by mass, and 5 parts by mass of a methyl methacrylate monomer was changed to 10 parts by mass of methacrylic acid, and a rectangular solid-shaped resin block having a thickness of 30 mm was fabricated. The material of the obtained resin block is a methyl methacrylate-methacrylic acid copolymer (hereinafter referred to as "MMA-MAA copolymer").

Similar operation to Example 1A was carried out, except that "Kanase Lite" in Example 1A was changed to the above-described resin block.

The results are shown in the following Table 4.

Example 4B

Similar operation to Example 2B was carried out, except that "MUX-60" in Example 2B was changed to "M-521" having the same mass.

Here, "M-521" is "KANE ACE (trademark) M-521" manufactured by Kaneka Corporation and is a rubber obtained by graft polymerization of a butadiene (co)polymer, which is a rubbery polymer having a cross-linked structure, with a thermoplastic resin component.

TABLE 3

| | | | Example 1B | Example 2B | Example 3B |
|---|---|---|---|---|---|
| Material for denture base | | Material | PMMA + rubber | PMMA + rubber | PMMA + rubber |
| | | Brand or manufacturing method | Add 2 wt % of MUX-60 | Add 4 wt % of MUX-60 | Add 6 wt % of MUX-60 |
| | Three-point flexural test | Flexural strength [MPa] | 115 | 109 | 103 |
| | | Flexural modulus [MPa] | 2922 | 2785 | 2775 |
| | Charpy impact test | Impact strength [kJ/m$^2$] | 2.56 | 2.79 | 4.42 |
| | | Angle [°] | 122.2 | 119.9 | 107.6 |
| | Molecular weight | Mw | 3,040,000 | 3,650,000 | 3,000,000 |
| | | Mn | 580,000 | 780,000 | 630,000 |
| | | Mw/Mn | 5.3 | 4.7 | 4.8 |
| | | Cutting workability | A | A | A |
| | Method of manufacturing denture base | | Cutting | Cutting | Cutting |
| Evaluation of denture base | Compression test | Yield point strength [kN] | 1.7 | 2.3 | 2.0 |

—Description of Table 3—

MUX-60 is a rubber obtained by graft polymerization of a butadiene (co)polymer, which is a rubbery polymer having a cross-linked structure, with a thermoplastic resin component.

As shown in Table 3, the denture bases manufactured by using the materials for a denture base in Examples 1B to 3B The results are shown in the following Table 4.

Example 5B

Similar operation to Example 2B was carried out, except that "MUX-60" in Example 2B was changed to "W-450" having the same mass.

Here, "W-450" is "Metablen (trademark) W-450" manufactured by Mitsubishi Rayon Co., Ltd. and is a rubber obtained by graft polymerization of an acrylic (co)polymer, which is a rubbery polymer having a cross-linked structure, with a thermoplastic resin component.

The results are shown in the following Table 4.

Example 6B

Similar operation to Example 2B was carried out, except that "MUX-60" in Example 2B was changed to "S-2001" having the same mass.

Here, "S-2001" is "Metablen (trademark) S-2001" manufactured by Mitsubishi Rayon Co., Ltd. and is a rubber obtained by graft polymerization of a silicone-based polymer with a thermoplastic resin component.

The results are shown in the following Table 4.

Example 3D

Similar operation to Example 1A was carried out, except that "Kanase Lite" in Example 1A was changed to a resin block ("Radel R5000" manufactured by Solvay Specialty Polymers Japan Co., Ltd.; the shape was a rectangular solid shape having a thickness of 30 mm) formed of polyphenyl sulfone (PPSU) which was the material for a denture base in the second embodiment.

The results are shown in the following Table 4.

Comparative Example 7

A resin block was fabricated as follows, using Acron Clear No. 5 (manufactured by GC CO., LTD.) as a raw material.

60 parts by mass of the powder material of Acron Clear No. 5 and 25 parts by mass of the liquid material thereof were weighed into a container and then mixed with each other. When the obtained mixture was left for a while to be changed to a rice cake-like state, the rice cake-like mixture was supplied into a previously provided acrylic mold (having a rectangular solid shape having an inner size of 120 mm×130 mm×35 mm) in which a polyolefin film was placed inside, and the mold was lidded. Subsequently, after this mold was put into an autoclave containing water, the inside of the autoclave was pressurized. The pressurized autoclave was slowly heated to 100° C. for 60 minutes or more. Heating was continued after the temperature of the autoclave reached 100° C., and the temperature of the autoclave was maintained at 100° C. for 30 to 40 minutes. Subsequently, heating of the autoclave was terminated, and the autoclave was cooled to 30° C.

Then, the pressure inside the autoclave was returned to normal pressure. The mold was taken out from the autoclave, and a finished block was taken out from the mold. The block was polished to obtain a rectangular solid-shaped resin block having a size of 110 mm×120 mm×30 mm.

Then, similar operation to Example 1A was carried out, except that "Kanase Lite" in Example 1A was changed to the above-described resin block. However, the three-point flexural test and the Charpy impact test were omitted.

The results are shown in the following Table 4.

Comparative Example 8

Similar operation to Comparative Example 7 was carried out, except that Acron Clear No. 5 (manufactured by GC CO., LTD.) in Comparative Example 7 was changed to Acron Live Pink No. 8 (manufactured by GC CO., LTD.).

The results are shown in the following Table 4.

TABLE 4

|  |  |  | Example 1C | Example 4B | Example 5B | Example 6B | Example 3D | Comparative Example 7 | Comparative Example 8 |
|---|---|---|---|---|---|---|---|---|---|
| Material for denture base | Material |  | MMA-MAA copolymer | PMMA + rubber | PMMA + rubber | PMMA + rubber | PPSU | PMMA | PMMA |
|  | Brand or manufacturing method |  | MMA-MAA copolymer (MAA 10 wt %) | Add 4 wt % of M-521 | Add 4 wt % of M-450 | Add 4 wt % of S-2001 | Radel R5000 | Acron Clear No. 5 | Acron Live Pink No. 8 |
|  | Three-point flexural test | Flexural strength [MPa] | 139 | 104 | 103 | 105 | 111 | N.D. | N.D. |
|  |  | Flexural modulus [MPa] | 3585 | 2722 | 2755 | 2784 | 2168 | N.D. | N.D. |
|  | Charpy impact test | Impact strength [kJ/m²] | 1.51 | 4.40 | 2.73 | 3.16 | 10.79 | N.D. | N.D. |
|  |  | Angle [°] | 132 | 109 | 122 | 118 | 63 | N.D. | N.D. |
|  | Molecular weight | Mw | 1,220,000 | 4,540,000 | 4,410,000 | 4,610,000 | N.D. | 990,000 | 1,000,000 |
|  |  | Mn | 230,000 | 710,000 | 290,000 | 340,000 | N.D. | 160,000 | 170,000 |
|  |  | Mw/Mn | 5.4 | 6.4 | 15 | 14 | N.D. | 6.3 | 6.0 |
|  | Cutting workability |  | A | A | A | A | A | B | B |
| Method of manufacturing denture base | Cutting |  | Cutting | Cutting | Cutting | Cutting | Cutting | Cutting | Cutting |
| Evaluation of denture base | Compression test | Yield point strength [kN] | 2.7 | 2.5 | 1.4 | 2.5 | 2.5 | 1.2 | 1.0 |

—Description of Table 4—

M-521 is a rubber obtained by graft polymerization of a butadiene (co)polymer with a thermoplastic resin component.

W-450 is a rubber obtained by graft polymerization of an acrylic (co)polymer with a thermoplastic resin component.

S-2001 is a rubber obtained by graft polymerization of a silicone-based polymer with a thermoplastic resin component.

As shown in Table 4, the denture bases manufactured by using the materials for a denture base in the respective Examples were all excellent in the durability (yield point strength) as compared to the denture bases in Comparative Examples 1 to 8 (Comparative Examples 1 to 6 are shown in Table 2). In addition, the materials for a denture base in the respective Examples were excellent in the cutting workability. Among the respective Examples, the denture bases in Examples 1C, 4B, 6B, and 3D were particularly excellent in the durability (yield point strength).

As compared to each Example, in the denture bases manufactured by using the materials for a denture base in Comparative Examples 7 and 8 having the Mw of less than 120 and formed of PMMA, the durability (yield point strength) was low. Further, as compared to the material for a denture base in each Example, the materials for a denture base in Comparative Examples 7 and 8 were inferior in the cutting workability (namely, at least one of cracking and chipping occurs during cutting).

Reference Example 1

As Reference Example 1, based on a denture base, there is shown an example of a method of estimating the flexural strength of a material for a denture base used as a raw material of the denture base.

It is practically difficult to cut out a test piece having a length of 80 mm, a width of 10 mm, and a thickness of 4 mm from the denture base.

However, when a minute flexural test of the denture base is conducted as follows, the flexural strength of the material for a denture base used as a raw material of the denture base can be estimated.

—Minute Flexural Test—

A minute test piece having a length of 25 mm, a width of 2 mm, and a thickness of 2 mm was cut out from a denture base, and a three-point flexural test of the obtained minute test piece was conducted under the conditions of a testing speed of 1 mm/min and a length of the support span of 20 mm. This three-point flexural test is referred to as the "minute flexural test", and the obtained flexural strength is referred to as "minute flexural strength".

Among the measurement conditions of the "minute flexural test", conditions other than the above conditions are similar to the conditions in the three-point flexural test of the material for a denture base.

Regarding the denture bases in Examples 1A, 1B, 2B, 3B, 1D, and 2D, the minute flexural strength was measured.

The obtained results are shown in the following Table 5.

The following Table 5 also shows the flexural strength of the material for a denture base in each Example.

TABLE 5

|  | Minute flexural strength of denture base [MPa] | Flexural strength of material for denture base [MPa] |
| --- | --- | --- |
| Example 1A | 116 | 121 |
| Example 1B | 108 | 115 |
| Example 2B | 102 | 109 |
| Example 3B | 95 | 103 |
| Example 1D | 115 | 122 |
| Example 2D | 165 | 188 |

FIG. 2 is a graph showing a relationship between the minute flexural strength of the denture base and the flexural strength of the material for a denture base and created based on the results of Table 5.

As seen in FIG. 2, the flexural strength of the material for a denture base is directly proportional to the minute flexural strength of the denture base. Accordingly, it is found that the flexural strength of the material for a denture base used as a raw material of the denture base can be estimated by measuring the minute flexural strength of the denture base.

It is assumed from the graph of FIG. 2 that for example, a denture base having a minute flexural strength of 95 MPa or more is manufactured using, as a raw material, a material for a denture base having flexural strength of 100 MPa or more. It is expected that the denture base having a minute flexural strength of 95 MPa or more is a denture base excellent in the durability (yield point strength in a compression test).

Reference Example 2

As Reference Example 2, based on a denture base, there is shown an example of a method of estimating the impact strength (Charpy impact strength) of a material for a denture base used as a raw material of the denture base.

It is practically difficult to cut out a single-notched test piece having a length of 80 mm, a width of 10 mm, a remaining width of 8 mm, and a thickness of 4 mm from the denture base.

However, when a minute impact test of the denture base is conducted as follows, the impact strength (Charpy impact strength) of the material for a denture base used as a raw material of the denture base can be estimated.

—Minute Impact Test—

A minute test piece having a length of 25 mm, a width of 2 mm, and a thickness of 2 mm was cut out from a denture base. A Dynstat impact test of the obtained minute test piece was conducted using a new Dynstat tester manufactured by Toyo Seiki Seisaku-Sho Ltd. under the conditions of a hitting direction in flatwise verticality, hammer energy: 20 kgf cm, swing angle: 90°, elevated angle: 90°, and unnotched, such that the minute test piece was hit at a position of 7.5 mm above a lower end of the minute test piece.

The Dynstat impact test is referred to as the "minute impact test", and the obtained impact strength is referred to as the "minute impact strength".

Regarding the denture bases in Examples 3A, 1B, 2B, and 3B, the minute impact strength was measured.

The obtained results are shown in the following Table 6.

The following Table 6 also shows the impact strength of the material for a denture base in each Example.

TABLE 6

|  | Minute impact strength of denture base [kJ/m$^2$] | Impact strength of material for denture base [kJ/m$^2$] |
| --- | --- | --- |
| Example 3A | 10.1 | 1.52 |
| Example 1B | 14.7 | 2.56 |
| Example 2B | 34.5 | 2.79 |
| Example 3B | 38.8 | 4.42 |

FIG. 3 is a graph showing a relationship between the minute impact strength of the denture base and the impact strength of the material for a denture base and created based on the results of Table 6.

As seen in FIG. 3, the impact strength of the material for a denture base is directly proportional to the minute impact strength of the denture base. Accordingly, it is found that the impact strength of the material for a denture base used as a raw material of the denture base can be estimated by measuring the minute impact strength of the denture base.

It is assumed from the graph of FIG. 3 that for example, a denture base having minute impact strength of 13 kJ/m$^2$ or more is manufactured using, as a raw material, a material for a denture base having impact strength of 2.0 kJ/m$^2$ or more. It is expected that the denture base having a minute impact strength of 13 kJ/m$^2$ or more is a denture base excellent in the impact resistance.

The entire disclosure of Japanese Patent Applications Nos. 2014-020634 and 2014-265370 are incorporated by reference in this specification.

All contents of the documents, patent applications, and technical standards described in this specification are incorporated herein by reference to the same extent as that when it is specifically and individually described that the respective documents, patent applications, and the technical standards are incorporated herein by reference.

The invention claimed is:

1. A material for a denture base containing a polymer component, the polymer component having a weight average molecular weight of 1,200,000 or more and containing an acrylic resin,
    wherein the acrylic resin is a polymer obtained by polymerizing a monomer component comprising 95% by mass or more of at least one selected from the group consisting of methacrylic acid and methacrylic acid alkyl ester, and
    wherein a content of the acrylic resin is 95% by mass or more based on a total amount of the material for a denture base.

2. The material for a denture base according to claim 1, wherein the weight average molecular weight of the polymer component is 1,500,000 or more.

3. The material for a denture base according to claim 1, wherein the weight average molecular weight of the polymer component is 2,500,000 or more.

4. The material for a denture base according to claim 1, wherein when the material for a denture base is formed into a test piece having a length of 80 mm, a width of 10 mm, and a thickness of 4 mm, the test piece exhibits 110 MPa or more of flexural strength measured by a three-point flexural test in accordance with JIS K7171 (2008) under conditions of a testing speed of 2 mm/min and a length of a support span of 64 mm.

5. The material for a denture base according to claim 4, wherein the flexural strength is 200MPa or less.

6. The material for a denture base according to claim 1, wherein when the material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm, the test piece exhibits 1.41 kJ/m$^2$ or more of impact strength measured by Charpy impact test under the condition of edgewise impact in accordance with JIS K7111-1 (2012).

7. The material for a denture base according to claim 1, wherein when the material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm, the test piece exhibits 2.0 kJ/m$^2$ or more of impact strength measured by Charpy impact test under the condition of edgewise impact in accordance with JIS K7111-1 (2012), and when the material for a denture base is formed into a test piece having a length of 80 mm, a width of 10 mm, and a thickness of 4 mm, the test piece exhibits 100 MPa or more of flexural strength measured by a three-point flexural test in accordance with JIS K7171 (2008) under conditions of a testing speed of 2 mm/min and a length of a support span of 64 mm.

8. The material for a denture base according to claim 7, wherein the polymer component further contains a rubber.

9. The material for a denture base according to claim 8, wherein the rubber contains a polymer obtained by graft polymerization of a rubbery polymer having a cross-linked structure with a thermoplastic resin component.

10. The material for a denture base according to claim 8, wherein the rubber contains a polymer obtained by graft polymerization of a butadiene (co)polymer with a thermoplastic resin component.

11. The material for a denture base according to claim 8, wherein a content of the rubber is from 1% by mass to 4% by mass based on a total amount of the material for a denture base.

12. The material for a denture base according to claim 8, wherein a content of the rubber is from 1% by mass to 2% by mass based on a total amount of the material for a denture base.

13. The material for a denture base according to claim 1, wherein:
    the monofunctional acrylic monomer consists of methacrylic acid and methacrylic acid alkyl ester, and
    an amount of the methacrylic acid is from 0.1% by mass to 15% by mass based on a total amount of the methacrylic acid and the methacrylic acid alkyl ester.

14. The material for a denture base according to claim 1, wherein the acrylic resin is polymethyl methacrylate.

15. A material for a denture base, wherein:
    when the material for a denture base is formed into a test piece having a length of 80 mm, a width of 10 mm, and a thickness of 4 mm, the test piece exhibits 110 MPa or more of flexural strength measured by a three-point flexural test in accordance with JIS K7171 (2008) under conditions of a testing speed of 2 mm/min and a length of a support span of 64 mm,
    the material for a denture base contains a polymer component that is at least one selected from the group consisting of a sulfone-based resin and an ether ketone resin; and
    a content of the polymer component is 90% by mass or more based on a total amount of the material for a denture base.

16. The material for a denture base according to claim 15, wherein the flexural strength is 200 MPa or less.

17. The material for a denture base according to claim 15, wherein when the material for a denture base is formed into a single-notched test piece which is provided with a notch having the shape A prescribed by JIS K7111-1 (2012) and has a length of 80 mm, a width of 10 mm, a remaining width of 8 mm, and a thickness of 4 mm, the test piece exhibits 1.41 kJ/m$^2$ or more of impact strength measured by Charpy impact test under the condition of edgewise impact in accordance with JIS K7111-1 (2012).

18. The material for a denture base according to claim 15, wherein the polymer component is at least one selected from the group consisting of polyphenyl sulfone and polyether ether ketone.

19. The material for a denture base according to claim 1, wherein a content of inorganic fibers and inorganic whiskers is 0.5% by mass or less, based on the total amount of the material for a denture base.

20. The material for a denture base according to claim 1, wherein the material for a denture base is a block body having a thickness of from 10 mm to 40 mm.

21. The material for a denture base according to claim 20, wherein the material for a denture base is used in manufacturing a denture base by cutting.

22. A denture base containing the material for a denture base according to claim 1.

23. A denture base obtained by cutting the material for a denture base according to claim 20.

24. A plate denture comprising the denture base according to claim 22 and an artificial tooth fixed to the denture base.

25. A method of manufacturing a denture base comprising a step of cutting the material for a denture base according to claim 20 to obtain a denture base.

26. The denture base manufacturing method according to claim 25, wherein the cutting step is a step of cutting the material for a denture base with the use of a CAD/CAM system to obtain a denture base.

27. A method of manufacturing a plate denture comprising:
- a step of cutting the material for a denture base according to claim 20 to obtain a denture base; and
- a step of fixing an artificial tooth to the denture base.

* * * * *